United States Patent [19]

Shinohara et al.

[11] Patent Number: 5,861,537
[45] Date of Patent: Jan. 19, 1999

[54] METHOD OF PRODUCING HIGH-QUALITY POLYETHYLENEPOLYAMINES

[75] Inventors: Shunya Shinohara, Shinnanyo; Sadakatsu Kumoi, Hikari, both of Japan

[73] Assignees: Tosoh Corporation, Shinnanyo, Japan; Delamine bv, Amersfoort, Netherlands

[21] Appl. No.: 906,244

[22] Filed: Aug. 4, 1997

[30] Foreign Application Priority Data

Aug. 5, 1996 [JP] Japan ................................. 8-221813

[51] Int. Cl.$^6$ ................................. C07C 209/84
[52] U.S. Cl. ................................. 564/498; 564/497
[58] Field of Search ................................. 564/493, 497, 564/498

[56] References Cited

U.S. PATENT DOCUMENTS 5,364,971 11/1994 Su et al. ................................. 564/498

FOREIGN PATENT DOCUMENTS 50-20047 7/1975 Japan .
3-38261 6/1991 Japan .

*Primary Examiner*—Brian M. Burn
*Attorney, Agent, or Firm*—Oblon, Spivak, McClelland, Maier & Neustadt, P.C.

[57] ABSTRACT

The invention provides a method of industrially producing high-quality polyethylenepolyamines, which exerts high decolorizing effect and is economical, comprising the steps that hydrogen halide is added to a mixture of polyethylene-polyamines and heated, then distillation is performed to fractionate components each having a boiling point not higher than that of triethylenetetramine, next alkali metal hydroxide is added to that residual liquor after distillation to neutralize, and distillation is performed again to fractionate components each having a boiling point not lower than that of tetraethylenepentamine.

7 Claims, No Drawings

METHOD OF PRODUCING HIGH-QUALITY POLYETHYLENEPOLYAMINES

BACKGROUND OF THE INVENTION

The present invention relates to a method of producing high-quality polyethylenepolyamines, in particular, decolorized high-quality polyethylenepolyamines.

Polyethylenepolyamine is a useful amine compound to be used for paper strength resin, epoxy-curing agent, lubricating oil additive, surfactant, etc. in large quantities.

Polyethylenepolyamines (hereinafter abbreviated as polyamines) are produced through a reaction between ethylene dichloride (hereinafter abbreviated as EDC) and ammonia and/or relatively lower ethyleneamines such as ethylenediamine (hereinafter abbreviated as EDA) or a reaction between ethanolamines and ammonia and/or relatively lower ethyleneamines such as EDA.

The polyamines obtained through these producing processes are usually mixtures and fractionated by distillation, but their distilled fractions have yellowish brown to dark brown color. This is considered to be due to the impurities, leading to decreased commercial value, if left as they are.

As the measures for solving this coloring problem, a lot of decolorizing methods of polyamines have been proposed.

For example, methods of using metal or its salt such as a method of treating polyamines with potassium hydroxide (specification of U.S. Pat. No. 3,595,921), a method of adding reducible metal like zinc, tin or aluminum and sodium hydroxide or potassium hydroxide to polyamines to treat under heat (Japanese Patent Publication No. Sho 44-2209), a method of adding Zinc and water to polyamine at room temperature to 150° C. to treat (Japanese Patent Publication No. Sho 44-4768) and a method of simply adding zinc alone to treat under heat (Japanese Patent Publication No. Sho 45-33163) are disclosed, moreover methods of using activated carbon or ion exchange resin such as a method of treating polyamine with activated carbon at high temperature (specification of U.S. Pat. No. 3,723,529) and a method of treating with-sulfonic acid type cation exchange resin (specification of U.S. Pat. No. 4,731, 165) are disclosed, and further methods of hydrogenating with catalyst such as a method of treating with acidic zeolite (specification of U.S. Pat. No. 4,737,243) and a method of hydrogenating using nickel, cobalt, palladium or ruthenium as a catalyst (Japanese Unexamined Patent Publication No. Sho 63-101421), and the like are disclosed.

However, all of these methods exert no sufficient decolorizing effect and are not satisfied industrially.

Namely, in the methods of using metal or its salt, expenses for metal run up, leading to disadvantage economically, metal or its salt accompanies with polyamines, thus requiring removal thereof, polyamines are contaminated reversely with metal dissolved out, and the like, hence they cannot be said to be industrial methods. In the methods of using activated carbon or ion exchange resin, deactivation thereof is significant and it is needed in large quantities, which are uneconomical. Also, in the methods of hydrogenating with catalyst, deactivation of catalyst is significant and it is needed in large quantities, which are uneconomical, and there is a danger of lowering the quality of polyamines by decomposed products, hence these also cannot become industrial methods.

For this reason, decolorizing methods of adding hydrochloric acid are proposed. For example, in Japanese Patent Publication No. Sho 50-20047, a method of distilling polyamines in the presence of their hydrochloride is disclosed, and, in Japanese Unexamined Patent Publication No. Sho 57-171939, a method of treating polyamines with their hydrochloride under heat in the presence of water followed by flush evaporation is disclosed.

However, despite that the method described in Japanese Patent Publication No. Sho 50-20047 is relatively economical and decolorizing effect is also not insignificant, large quantities of hydrochloric acid are needed and salt is produced in large quantities as well by neutralization, hence it is not a satisfiable method industrially. Also, the method described in Japanese Unexamined Patent Publication No. Sho 57-171939 exerts relatively high decolorizing effect, but coexistence of low-boiling point water at high temperature brings about high pressure, thus requiring a device endurable pressure. In addition, polyamines obtained by flush evaporation are not of single component and much of low-boiling point components and high-boiling point-components are accompanied, hence they cannot become merchandise if left as they are, requiring to distill again for separation, which cannot be said to be economical method.

As descried above, all of the conventional methods are not ones that effectively and efficiently decolorize polyamine and produce high-quality polyamine, hence they were not satisfiable.

The invention was made in view of the subjects aforementioned, and the purpose is to provide an industrial producing method that exerts high decolorizing effect and affords high-quality polyamines economically.

The inventors investigated diligently on a method of producing high-quality polyamines, concretely on an economical and industrial decolorizing method.

As a result, it was seen that, for economically obtaining high-quality polyamine, concretely, sufficiently decolorized polyamine, a decolorizing method adding-hydrochloric acid was effective. When obtaining polyamines by distillation, however, high-boiling point polyamines could not be decolorized sufficiently, though low-boiling point polyamines were decolorized sufficiently.

There, as a result of further investigations, it was seen that, at the point of time when low-boiling point polyamines had been separated by distillation, alkali metal hydroxide was added to residual liquor after distillation to once neutralize hydrochloric acid existing in the residual liquor after distillation and then distillation was performed again to separate high-boiling point polyamines, thereby all polyamines from low-boiling point polyamines to high-boiling point polyamines could be obtained in the state of being sufficiently decolorized.

Moreover, it was seen that, when using halogen acids such as hydrobromic acid and hydroiodic acid in place of hydrochloric acid to be added, same or higher decolorizing effect than that with hydrochloric acid could be obtained.

From the investigation results as above, it has been found that the subjects aforementioned can be solved and the goal can be accomplished by treating polyamine under heat in the presence of halogen acid, then performing distillation to separate low-boiling point polyamines, next, adding alkali to the residual liquor after distillation to neutralize and performing distillation again to separate high-boiling point polyamines, leading to the completion of the invention at last.

SUMMARY OF THE INVENTION

The invention relates to a method of producing high-quality polyamines characterized in that hydrogen halide is added to a mixture of polyamines and treated under heat, then distillation is performed to fractionate components each having a boiling point not higher than that of triethylenetetramine, next alkali metal hydroxide is added to the residual liquor after distillation, and distillation is performed again to fractionate components each having a boiling point not lower than that of tetraethylenepentamine.

The gist of the invention lies in that,

① hydrogen halide is added to a mixture of polyamines followed by heating,

② low-boiling point polyamine components are separated by distillation in the presence of halogen acid, and ③ alkali metal hydroxide is added to the residual liquor after distillation to neutralize previously added halogen acid and then high-boiling point polyamine components in said residual liquor after distillation are separated by distillation.

By the method of the invention, highly decolorized high-quality polyamines can be produced effectively and economically by means of simple procedures.

DETAILED DESCRIPTION OF THE INVENTION

In following, the invention will be explained in more detail.

In the invention, polyamines refer to ethyleneamines each having a boiling point not lower than that of piperazine. The boiling points of ethyleneamines correlate to the molecular weights and, in order of boiling point from low, there are ethylenediamine [hereinafter abbreviated as EDA, b.p. 116.9° C. (760 mmHg)], piperazine [hereinafter abbreviated as PIP, b.p. 148.5° C. (760 mmHg)], diethylenetriamine [hereinafter abbreviated as DETA, b.p. 206.9° C. (760 mmHg)], N-aminoethylpiperazine [hereinafter abbreviated as N-AEP, b.p. 222° C. (760 mmHg)], triethylenetetramine [hereinafter abbreviated as TETA, b.p. 277.4° C. (760 mmHg)], tetraethylenepentamine [hereinafter abbreviated as TEPA, b.p. 195° C. (10 mmHg)], pentaethylenehexamine [hereinafter abbreviated as PEHA, b.p. 230° C. (10 mmHg)], hexaethyleneheptamine (hereinafter abbreviated as HEPA), etc. These are usually produced through a reaction between EDC and ammonia and/or ethyleneamines (EDC process), a reaction between ethanolamines and ammonia and/or ethyleneamines (EO process), a reaction between formalin, cyanic acid and ammonia and/or ethyleneamines, and the like, and separated by distillation for commercialization. All of them have a boiling point of 100° C. or higher, hence they are usually fractionated by distillation under reduced pressure. Besides, in the invention, polyamines each having a boiling point not lower than that of PIP and not higher than that of TETA are sometimes referred to low-boiling point polyamines and polyamines each having a boiling point not lower than that of TEPA to high-boiling point polyamines.

The method of the invention is applied suitably to ethyleneamines each having a molecular weight (boiling point) not lower than that of DETA produced through said EDC process or EO process. Ethyleneamines each having a molecular weight lower than that of DETA can afford high-quality products only by distillation, thus requiring no decolorizing treatment in many cases. Whereas, ethyleneamines each having a molecular weight higher than that of DETA have much coloring impurities and these cannot be removed only by distillation, hence decolorizing treatment is necessary and indispensable.

As the mixtures of polyamines to be used for the method of the invention, for example, ① a mixture of various ethyleneamines obtainable through said reactions, ② a residual liquor after separated EDA or ethyleneamines each having a boiling point not lower than that of EDA and not higher than that of N-AEP from ① by distillation (that is, mixture of relatively high-boiling point polyamines such as TETA, TEPA and PEHA), ③ each fraction such as TETA, TEPA or PEHA or their mixture obtainable by distillation of ① or ②, and the like are mentioned, all of which can be used suitably for the method of the invention.

The method of the invention is not undergone the restraint due to the existence of water and inorganic salts of any rate. Ordinarily, when offering a mixture of ethyleneamines obtained through the reaction between EDC and ammonia to the method of the invention, water and inorganic salts such as NaCl are present in its raw material, but polyamines can be decolorized effectively without any problem. Moreover, in the case of polyamines, from the mixture of which relatively low-boiling point ethyleneamines were separated by distillation, no water is present in the raw material, but polyamines can be decolorized effectively also in this case according to the invention. Furthermore, also when neither water nor inorganic salts are present as the case of each fraction such as TETA, TEPA or PEHA or their mixture obtainable-by distillation, polyamines can be decolorized suitably. Still more, alkanolamines may be contained in polyamine, and, in this case, too, polyamines can be decolorized effectively by the method of the invention.

For the method of the invention, it is essential to add hydrogen halide to the mixture of polyamines aforementioned.

As the hydrogen halides, hydrogen chloride, hydrogen bromide, hydrogen iodide and hydrogen fluoride are mentioned, and one type thereamong may be used or two or more types may be used. Because of its dangerous property and slightly poor effect as well, hydrofluoric acid is difficult to handle, which cannot be said to be so suitable for use in the industrial producing method. Other three types all afford sufficient decolorizing effect, but the effect on the basis of mole is highest for hydrogen iodide and the effect on the basis of weight is highest for hydrogen bromide. On the other hand, from economical aspect, hydrogen chloride is preferable.

The method of adding hydrogen halide is not particularly restricted, and a method of blowing hydrogen halide into polyamines as a gas, a method of adding aqueous solution of hydrogen halide to polyamines to produce salt of polyamine, a method of directly adding salt of polyamines with halogen acid that was prepared beforehand to polyamines, and the like are used. Generally, the method of adding aqueous solution of hydrogen halide is economical and the procedure is easy, which is desirable. Moreover, the concentration of aqueous solution of halogen acid to be added is not restricted at any rate.

The addition level of hydrogen halide depends on the concentration of coloring components of polyamines to be offered to decolorizing treatment. Ordinarily, in the case of hydrochloric acid, it is 0.05 to 10% by weight, preferably 0.1 to 5% by-weight as HCl on polyamines. When the addition level is remarkably low, the decolorizing effect decreases, and, when the addition level is remarkably high, the decolorizing treatment can be performed for a short time, but the decomposition of polyamine takes place partially and the corrosion of material of device poses a problem.

For the method of the invention, heating treatment of the mixture of polyamines in the presence of hydrogen halide is essential as a pretreatment for distilling purification.

The heating temperature is usually within a range from 150° to 240° C. and the decolorizing treatment can be performed suitably in this temperature range, but, further preferably, it is within a range from 170° to 230° C. When the heating temperature is remarkably low, it takes a long time for decolorization, and, when the heating temperature is remarkably high, decolorization can be performed for a short time, but the problems of decomposition of polyamines, corrosion of device and the like are caused.

The pressure at the time of heating treatment is not particularly restricted and the treatment can be implemented easily under either atmospheric pressure or reduced pressure. When implementing under reduced pressure, the heating treatment can be performed while distilling off the components each having a boiling point not higher than that of DETA, which is rational and economical. By this method, the operating time for distillation can be reduced drastically.

The time required for the heating treatment depends on the concentration of coloring components of polyamine to be offered to the decolorizing treatment, similarly to the case of addition level of hydrogen halide. Ordinarily, it is preferable to be 0.5 to 10 hours, further preferably 1 to 5 hours.

For the method of the invention, fractionation of components each having a boiling point not higher than that of TETA by distillation is essential, after heating treatment.

As described above, distillation of low-boiling point components and heating treatment may be performed concurrently, but it is preferable to perform the distillation of TETA after heating treatment. This is because of that polyamines each having a boiling point not lower than that of TETA are not undergone sufficient decolorizing effect by the heating treatment while distilling.

The distillation of low-boiling point components up to TETA is usually implemented as follows; ambient pressure in the case of PIP and reduced pressure as low as 5 to 100 mmHg in the cases of DETA, N-AEP and TETA. Moreover, the theoretical plate number on distillation is usually 5 to 60 plates and the reflux ratio is usually 0.5 to 10. By the procedures as above, colorless, very high-quality, low-boiling point polyamines can be obtained and the degree of coloration thereof is 10 or lower on APHA scale for DETA and 30 or lower on APHA scale for TETA.

For the method of the invention, it is essential that, after distillation of low-boiling point components of TETA and down, excess acid in that residual liquor after distillation is neutralized with alkali, and then distillation is performed again to fractionate high-boiling point components of TEPA and up. By this procedure, fully decolorized high-quality TEPA, PEHA and HEPA can be obtained.

In the invention, alkalies to be used for neutralizers are hydroxide of alkali metals. Concretely, sodium hydroxide and/or potassium hydroxide are preferable because of being easily operative and economical.

The method of adding alkali is not particularly restricted, but the addition of aqueous solution that is advantageous for neutralizing reaction is suitable.

The addition level of alkali is preferable to be within a range from −0.25 to +0.25 eq. (equivalent)/kg to the residual liquor after distillation from the aspect of distilled quality of TEPA, PEHA, etc.

As a method of measuring the concentration of acid in residual liquor after distillation at that time, usually, neutralizing titration technique is used. Concretely, part of residual liquor is diluted with water and excess amount of 1N aqueous solution of sodium hydroxide is added, which is back-titrated to determine the concentration of acid.

The distillation of components each having a boiling point not lower than that of TEPA is implemented usually at a pressure not higher than 10 mmHg. Moreover, the theoretical plate number on distillation is usually 1 to 30 plates and the reflux ratio is usually 0 to 5. In this way, colorless, very high-quality, high-boiling point polyamines can be obtained, and the degree of coloration is 2 or lower on Gardner scale for TEPA and 6 or lower on Gardner scale for PEHA When commercializing high-molecular weight polyamines contained in the residual liquor after distillation of TEPA and PEHA, it is required to make the addition of alkali more strict. This is because of that, due to increased amount of alkali metal halide or remaining halogen acid, the quality of that product is lowered. In the former case, alkali metal halide is usually deposited, thus, it can be removed in considerable proportion by the procedure of solid-liquid separation.

Followings are effects of the invention enumerated.

(1) Not only low-boiling point polyamines (PIP to TETA), but also high-boiling point polyamines (TEPA and up) that are difficult in decolorization can be decolorized effectively and efficiently.

(2) As for polyamines from low-boiling point to high-boiling point, high-quality polyamines can be produced in respective components.

(3) Since decomposition of polyamines can be suppressed, high-quality polyamines that contain little impurities such as alkylamine can be produced in high yield.

(4) The chemicals to be used for decolorization are halogen acid and alkali metal hydroxide, which is very economical.

(5) The procedures include only heating and distillation and the process is simple, which allow to easily implement industrially.

(6) By offering the residual liquor after distillation of PEHA being high-boiling point polyamine to solid-liquid separation, useful polyamines each having further higher molecular weight and higher boiling point can be obtained.

In following, the invention will be illustrated more concretely based on examples, but the invention is not confined to these.

Besides, for the evaluation of the chromaticity of polyamines, Gardner expression that measures with Gardner calorimeter according to ASTM D-1544 or APHA expression that uses Pt—Co color standards according to ASTM D-1209-62 was employed. In both of Gardner chromaticity and APHA chromaticity, yellowish brown color increases with increasing numeral value and Gardner chromaticity of 1 corresponds approximately to APHA chromaticity of 250.

PREPARATIVE EXAMPLE

Low-boiling point components were removed by distilling a mixture of crude polyamines produced through EDC process, thereby a mixture of polyamines with Gardner number of 8, containing 9.8% by weight of components each having a boiling point not higher than that of DETA, 53.0% by weight of TETA, 23.2% by weight of TEPA, 10.2% by weight of components each having a boiling point not lower than that of PEHA, 1.3% by weight of $H_2O$ and 2.5% by weight of NaCl was obtained.

EXAMPLE 1

Into a 1 L four-neck round-bottom flask equipped with Older-show distilling tower (5 plates), thermometer, insert pipe and stirrer adaptable to vacuum, 500 g of the mixture of polyamines obtained in Preparative example were charged, and 10 g of 35% hydrochloric acid (0.096 mol) were slowly added dropwise while stirring.

After dropwise addition, the inside of system was replaced enough with nitrogen and pressure was decreased to 150 mmHg with vacuum pump, then the temperature of mixed liquor was raised with mantle heater.

With an increase in the temperature of liquor, low-boiling point components were distilled off at a reflux ratio of 1, and the temperature of liquor was further raised. After start of heating, the distillation of DETA fraction began at about 1 hour later, and, at that time, the temperature of liquor was 215° C. and the temperature at the top of tower was 140° C.

DETA fraction was distilled off for 3 hours (heating treatment for 3 hours) at a reflux ratio of 1. At the point of time when heating treatment for 3 hours was ended, the temperature of liquor was 225° C. and the temperature of the top of tower was 145° C. After end of heating treatment, the content was cooled immediately, pressure was lowered to 8 mmHg, and, successively, remaining DETA fraction and TETA fraction were distilled off.

In this ways, 60.7 g of fraction having a boiling point not higher than that of DETA, 221.1 g of TETA fraction and 222.9 g of residual liquor were obtained.

Further, a liquor that was neutralized with 48% NaOH added to 70 g of residual liquor was charged into a 100 cc round-bottom flask and distilled at 1 mmHg to obtain 35.4 g of TEPA fraction.

Type of hydrogen halide, addition level of aqueous solution of hydrogen halide, conditions of heating treatment and the chromaticity of TETA and TEPA obtained are shown in Table 1.

similarly to Example 1. Type of hydrogen halide, addition level of aqueous solution of hydrogen halide, conditions of heating treatment and the chromaticity of TETA and TEPA obtained are shown together in Table 1. As evident from Table 1, little decolorized TETA and TEPA were obtainer.

EXAMPLE 2

Except that the heat treatment was performed for 1.5 hours, the decolorizing treatment was performed by the same procedure as in Example 1. Type of hydrogen halide, addition level of aqueous solution of hydrogen halide,- conditions of heating treatment and the chromaticity of TETA and TEPA obtained are shown together in Table 1.

EXAMPLE 3 AND EXAMPLE 4

Except that hydrogen halides shown in table 1 were added in amounts of 0.096 mol, the decolorizing treatments were performed by the same procedure as in Example 2. Type of hydrogen halide, addition level of aqueous solution of hydrogen halide, conditions of heating treatment and the chromaticity of TETA and TEPA obtained are shown together in Table 1.

EXAMPLE 5 THROUGH EXAMPLE 17

Except that reaction liquors shown in Table 2 were used, the decolorizing treatments of polyamines were performed similarly to Example 1. Type of hydrogen halide, addition level of aqueous solution of hydrogen halide, conditions of heating treatment and the chromaticity of TETA and TEPA obtained are shown in Table 2. Besides, in all of these

TABLE 1

| | Charge composition | | Conditions of heating treatment | | | Chromaticity of distilled fraction | |
|---|---|---|---|---|---|---|---|
| | Polyamines | Hydrogen halide | | Pressure | Temperature | Time | TETA | TEPA |
| | Charge/g | Type | Charge/g | mmHg | °C. | Hr | APHA | Gardner |
| Example 1 | 500 | 35% HCl | 10.0 | 150 | 220 | 3.0 | 15 | 0.5 |
| Comparative example 1 | 500 | — | — | 150 | 220 | 3.0 | 250 | 5 |
| Example 2 | 500 | 35% HCl | 10.0 | 150 | 220 | 1.5 | 30 | 1.0 |
| Example 3 | 500 | 47% HBr | 16.5 | 150 | 220 | 1.5 | 15 | 0.5 |
| Example 4 | 500 | 47% HI | 21.6 | 150 | 220 | 1.5 | 5 | <0.5 |

COMPARATIVE EXAMPLE 1

Except that no hydrochloric acid was added and no heating treatment was performed, distillation was performed examples, compositional problems such as cyclic/noncyclic amine ratio and impurities in TETA and TEPA fractions after distillation were not found at all.

TABLE 2

| | Charge composition | | | Conditions of heating treatment | | | Chromaticity of distilled fraction | |
|---|---|---|---|---|---|---|---|---|
| | Polyamines | Hydrogen halide | | Pressure | Temperature | Time | TETA | TEPA |
| | Charge/g | Type | Charge/g | mmHg | °C. | Hr | APHA | Gardner |
| Example 5 | 500 | 35% HCl | 2.5 | 150 | 220 | 1.5 | 80 | 1.5 |
| Example 6 | 500 | 35% HCl | 2.5 | 150 | 220 | 3.0 | 30 | 1.0 |
| Example 7 | 500 | 35% HCl | 5.0 | 150 | 220 | 1.5 | 30 | 1.0 |
| Example 8 | 500 | 35% HCl | 25.0 | 150 | 220 | 1.0 | 10 | <0.5 |
| Example 9 | 500 | 35% HCl | 10.0 | 30 | 175 | 1.5 | 100 | 2.0 |

TABLE 2-continued

| | Charge composition | | | Conditions of heating treatment | | | Chromaticity of distilled fraction | |
|---|---|---|---|---|---|---|---|---|
| | Polyamines | Hydrogen halide | | Pressure | Temperature | Time | TETA | TEPA |
| | Charge/g | Type | Charge/g | mmHg | °C. | Hr | APHA | Gardner |
| Example 10 | 500 | 35% HCl | 10.0 | 70 | 200 | 1.5 | 60 | 1.5 |
| Example 11 | 500 | 35% HCl | 10.0 | 200 | 235 | 1.5 | 15 | 0.5 |
| Example 12 | 500 | 35% HCl | 10.0 | 30 | 175 | 5.0 | 20 | 0.5 |
| Example 13 | 500 | 47% HBr | 8.3 | 150 | 220 | 1.5 | 20 | 0.5 |
| Example 14 | 500 | 47% HBr | 16.5 | 150 | 220 | 3.0 | 10 | <0.5 |
| Example 15 | 500 | 47% HBr | 16.5 | 30 | 175 | 3.0 | 30 | 1.0 |
| Example 16 | 500 | 57% HI | 10.3 | 150 | 220 | 1.5 | 10 | 0.5 |
| Example 17 | 500 | 57% HI | 21.6 | 30 | 175 | 3.0 | 30 | 0.5 |
| Example 18 | 500 | 35% HCl | 5.0 | 150 | 220 | 1.5 | 30 | 1.0 |
| Example 19 | 500 | 35% HCl | 10.0 | 30 | 175 | 3.0 | 20 | 0.5 |

EXAMPLE 18 AND EXAMPLE 19

Except that reactions were conducted under the conditions shown in Table 2 and the neutralization of residual liquors after distillation of TETA was made with 48% KOH, the decolorizing treatments of polyamines were performed similarly to Example 1. Type of hydrogen halide, addition level of aqueous solution of hydrogen halide, conditions of heating treatment and the chromaticity of TETA and TEPA obtained are shown together in table 2. Besides, in all of these examples, compositional problems such as cyclic/noncyclic amine ratio and impurities in TETA and TEPA fractions after distillation were not found at all.

COMPARATIVE EXAMPLE 2 THROUGH COMPARATIVE EXAMPLE 4

Except that reactions were conducted under the conditions ♥own in Table 3 and no hydrochloric acid was added, the decolorizing treatments of polyamines were performed similarly to Example 1. Type of hydrogen halide, addition level of aqueous solution of hydrogen halide, conditions of heating treatment and the chromaticity of TETA and TEPA obtained are shown in Table 3. As evident from Table 3, little decolorized TETA and TEPA were obtained.

COMPARATIVE EXAMPLE 5 AND COMPARATIVE EXAMPLE 6

Except that reactions were conducted under the conditions shown in Table 3 and no heating treatment was performed, the decolorizing treatments of polyamines were performed similarly to Example 1. Type of hydrogen halide, addition level of aqueous solution of hydrogen halide, conditions of heating treatment and the chromaticity of TETA and TEPA obtained are shown together in Table 3. As evident from Table 3, TETA and TEPA with low decolorizing effect were obtained.

What is claimed is:

1. A method of producing polyethylenepolyamines comprising the steps that hydrogen halide is added to a mixture of polyethylenepolyamines and heated, then distillation is performed to fractionate components each having a boiling point not higher than that of triethylenetetramine, next alkali metal hydroxide is added to that residual liquor after distillation to neutralize, and distillation is performed again to fractionate components each having a boiling point not lower than that of tetraethylenepentamine.

2. The method of claim 1, wherein hydrogen halide is at least one type selected from a group consisting of hydrochloric acid, hydrobromic acid and hydroiodic acid.

3. The method of claim 1, wherein heating temperature is 150° C. to 240° C.

4. The method of claim 1, wherein heating time is 1 to 5 hours.

TABLE 3

| | Charge composition | | | Conditions of heating treatment | | | Chromaticity of distilled fraction | |
|---|---|---|---|---|---|---|---|---|
| | Polyamines | Hydrogen halide | | Pressure | Temperature | Time | TETA | TEPA |
| | Charge/g | Type | Charge/g | mmHg | °C. | Hr | APHA | Gardner |
| Comparative example 2 | 500 | — | — | 30 | 175 | 1.5 | 300 | 4.5 |
| Comparative example 3 | 500 | — | — | 150 | 220 | 1.5 | 500 | 5.0 |
| Comparative example 4 | 500 | — | — | 200 | 235 | 1.5 | 550 | 5.0 |
| Comparative example 5 | 500 | 35% HCl | 10.0 | 150 | — | — | 170 | 3.0 |
| Comparative example 6 | 500 | 35% HCl | 25.0 | 150 | — | — | 120 | 2.0 |

5. The method of claim 1, wherein heating is performed under reduced pressure.

6. The method of claim 1, wherein the addition level of hydrogen halide is 0.05 to 10% by weight on polyethylenepolyamines.

7. The method of claim 1, wherein components each having a boiling point not lower than that of tetraethylenepentamine obtainable by distilling again is one or more kinds selected from a group consisting of tetraethylenepentamine, pentaethylenehexamine and hexaethyleneheptamine.

* * * * *